United States Patent
Georgi et al.

(10) Patent No.: US 8,663,083 B2
(45) Date of Patent: Mar. 4, 2014

(54) SYSTEM, METHOD, COMPUTER-READABLE MEDIUM, AND USE FOR PLANNING COMBINED THERAPY

(75) Inventors: Jens-Christoph Georgi, Aachen (DE); Bernd Schweizer, Herzogenrath (DE)

(73) Assignee: Koninklijke Philips N.V., Eindhoven (NL)

( * ) Notice: Subject to any disclaimer, the term of this patent is extended or adjusted under 35 U.S.C. 154(b) by 1253 days.

(21) Appl. No.: 12/517,717

(22) PCT Filed: Dec. 5, 2007

(86) PCT No.: PCT/IB2007/054924
§ 371 (c)(1),
(2), (4) Date: Jun. 4, 2009

(87) PCT Pub. No.: WO2008/068717
PCT Pub. Date: Jun. 12, 2008

(65) Prior Publication Data
US 2010/0081857 A1 Apr. 1, 2010

(30) Foreign Application Priority Data
Dec. 8, 2006 (EP) .................................... 06125697

(51) Int. Cl.
*A61N 5/00* (2006.01)
(52) U.S. Cl.
USPC .......................................................... 600/1
(58) Field of Classification Search
USPC ....................................................... 600/1–8
See application file for complete search history.

(56) References Cited

U.S. PATENT DOCUMENTS

| | | |
|---|---|---|
| 6,241,725 B1 | 6/2001 | Cosman |
| 2002/0040220 A1 | 4/2002 | Zvuloni et al. |
| 2004/0131587 A1 | 7/2004 | Thomas et al. |

OTHER PUBLICATIONS

Chang, I. A., et al.; Thermal modeling of lesion growth with radiofrequency ablation devices; 2004; BioMedical Engineering Online; 3:27.
Crezee, J., et al.; Experimental verification of bioheat transfer theories: measurement of temperature profiles around large artificial vessels in perfused tissue; 1990; Phys. Med. Biol.; 35(7)905-923.
McDannold, N. J., et al.; Microbubble Contrast Agent with Focused Ultrasound to Create Brain Lesions at Low Power Levels: MR imaging and Histologic Study in Rabbits; 2006; Radiology; 241(1)95-106.
Olsrud, J., et al.; MRI thermometry in phantoms by use of the proton resonance frequency shift method: application to interstitial laser thermotherapy; 1998; Phys. Med. Biol.; 43:2597-2613.
Erdi, A. K., et al.; Use of the fast Hartley transform for three-dimensional dose calculation in radionuclide therapy; 1998; Am. Assoc. Phys. Med.; 25(11)2226-2233.
Kinuya, S., et al.; Optimization of radioimmunotherapy interactions with hyperthermia; 2004; Int'l J. of Hyperthermia; 20(2)190-200.
Laitinen, J. O., et al.; The effect of three dimensional activity distribution on the dose planning of radioimmunotherapy for patients with advanced intraperitoneal pseudomyxoma; 1997; Cancer; 80(12)2545-2552.
Sgouros, G., et al.; Three-dimensional dosimetry for radioimmunotherapy treatment planning; 1993; Journal of Nuclear Medicine; 34(9)1595-1601.
Wan, H., et al.; Thermal dose optimization for ultrasound tissue ablation; 1999; IEEE Trans. on Ultrasonics, Ferroelectrics and Frequency Control; 46(4)913-928.

*Primary Examiner* — John Lacyk

(57) ABSTRACT

A system and method for planning a necrosis-inducing therapy and subsequent administration of a necrosis-targeting agent are described. The system takes into account the effect of necrosis-induction therapy as a basis for the biodistribution estimate of the necrosis-targeting agent. This interaction between the different calculation steps is essential for an accurate planning result. A computer-readable medium and use are also provided.

19 Claims, 3 Drawing Sheets

SYSTEM, METHOD, COMPUTER-READABLE MEDIUM, AND USE FOR PLANNING COMBINED THERAPY

FIELD OF THE INVENTION

This invention relates in general to the field of therapy planning and more particularly to combined treatment with a necrosis-inducing modality and necrosis-targeting agents.

BACKGROUND OF THE INVENTION

In the therapy of neoplasia (e.g. small tumors or cancer metastases) that are locally restricted, localized minimally invasive treatment options are an alternative to surgical resection. Many of these methods, such as high-intensity focused ultrasound (HIFU), radiofrequency ablation (RFA), cryo-surgery, laser ablation, and microwave ablation (MWA) are currently under development. In these methods, tissue containing the cancerous lesion is either overheated or overcooled, resulting in the uncontrolled death (coagulative necrosis) of up to 100% of the cells in the treated area.

Necrotic cells, in contrast to normal or apoptotic cells, show leaky membranes. This fact is exploited by a bio-molecular targeting mechanism currently in a clinical trial phase, the Tumor Necrosis Therapy (TNT), which may be used to deliver toxic payloads to necrotic areas. An example of this new approach is the monoclonal antibody 131I-chTNT-1/B (named COTARA®), which delivers a radioactive isotope (Iodine-131) for targeted radiotherapy (TRT) to the histone H1 in the nuclei of necrotic cells. The radioactivity emitted by the iodine isotope not only affects the targeted, dying, or already dead cells, but also adjacent living cells (by-stander or cross-fire effect).

A problem that a physician encounters when treating neoplasia of a patient is that, if a patient is in need of several therapy modalities, it is time consuming to perform a therapy planning for each modality. This may lead to prolonged discomfort for the patient.

Hence, an improved therapy planning system, method, computer-readable medium, and the use thereof would be advantageous as they provide increased treatment efficiency, flexibility, and cost-effectiveness.

SUMMARY OF THE INVENTION

Accordingly, the present invention preferably seeks to mitigate, alleviate, or eliminate one or more of the above-identified deficiencies in the art and disadvantages, singly or in any combination, and solves at least the above-mentioned problems by providing a system, method, computer-readable medium, and use according to the appended patent claims.

According to one aspect of the invention, there is provided a system for planning a combined necrosis-inducing and -targeting therapy of a patient. The system comprises a first calculation unit for calculating a predicted temperature distribution in the patient's tissue, a second calculation unit for calculating a necrosis probability map based on the predicted temperature distribution of the tissue, a third calculation unit for calculating a biodistribution map of a necrosis-targeting agent comprising a radioactive substance intended to be added to the tissue on the basis of the necrosis probability map, and a fourth calculation unit for calculating the radioactive dose distribution of the necrosis-targeting agent by convolving the biodistribution map with a convolution kernel specific to the necrosis-targeting agent.

According to another aspect of the invention, there is provided a method of planning a combined necrosis-inducing and -targeting therapy of a patient. The method comprises the steps of: calculating a predicted temperature distribution in the patient's tissue, calculating a necrosis probability map based on the predicted temperature distribution of the tissue, calculating a biodistribution map of a necrosis-targeting agent comprising a radioactive substance intended to be added to the tissue on the basis of the necrosis probability map, and calculating the radioactive dose distribution of the necrosis-targeting agent by convolving the biodistribution map with a convolution kernel specific to the necrosis-targeting agent.

According to a further aspect of the invention, there is provided a computer-readable medium having embodied thereon a computer program designed to be processed by a computer for planning a combined necrosis-inducing and -targeting therapy of a patient. The computer-readable medium comprises a first calculation code segment for calculating a predicted temperature distribution in the patient's tissue, a second calculation code segment for calculating a necrosis probability map based on the predicted temperature distribution of the tissue, a third calculation code segment for calculating a biodistribution map of a necrosis-targeting agent comprising a radioactive substance intended to be added to the tissue on the basis of the necrosis probability map, and a fourth calculation code segment for calculating the radioactive dose distribution of the necrosis-targeting agent by convolving the biodistribution map with a convolution kernel specific to the necrosis-targeting agent.

According to yet another aspect of the invention, there is provided a use of the system, method, or computer-readable medium for therapy planning in the treatment of cancer or neoplasia.

In cancer therapy, the combination of two treatments may have a better therapeutic effect than each of them alone in many cases of clinical oncology.

Predictive algorithms for use in therapy planning are currently available for both HC and TNT. In the case of HC the algorithms include calculation of temperature fields caused by the necrosis-inducing therapy, and in the case of TNT the algorithms are based on the calculation of the radiation dose absorbed in the tissue. However, there are currently no combined therapy planning methods for HC and TNT in which the therapy modalities are interconnected so as to optimize the treatment effect.

The present invention in some of its embodiments provides a treatment planning tool for use in the treatment of liver metastases which is a combination of necrosis-inducing therapy and a necrosis-targeting agent, i.e. a TNT agent, Although the effect of the necrosis-inducing treatment has a direct influence on the distribution of the necrosis-targeting agent, dedicated planning tools for a combined treatment are not available for most combined therapies at present. As a result, the treatment options are not optimally adapted to each other in clinical practice.

According to an embodiment, the generation of a biodistribution map from a predicted temperature distribution advantageously renders a prediction of the dosage of a necrosis-targeting agent possible.

Advantages of a combined therapy planning of necrosis-inducing therapy by overheating or overcooling, hereinafter denoted HC, and tumor necrosis therapy (TNT), denoted HC-TNT, are the possibility to optimize a therapy with respect to anti-tumor effects and the avoidance of side effects, which would be impossible without such planning.

An advantage of a combination therapy planning is that the target region for the antibody may be externally defined in a necrosis-inducing treatment session before the necrosis-targeting agent is applied. A combined treatment allows abundant binding sites for the monoclonal antibody in a sharply defined target volume, thus making a sharp radioactive dose distribution possible. Another advantage of combined therapy planning is the fact that cells surviving the necrosis induction, e.g. in the periphery of the tumor lesion, are killed by the additional radioactive dose from the targeted agent on the basis of the therapy planning.

The presented combined HC-TNT-therapy planning system, method, computer-readable medium, and use in some embodiments take into account the effect of necrosis induction by the HC-step as a basis for the biodistribution estimate of the TNT agent. This interaction between the different calculation steps is essential for an accurate planning result. The provided therapy planning system, method, computer-readable medium, and use provide a reduced discomfort for the treated patient, a higher treatment efficacy, and an increased flexibility and cost effectiveness.

BRIEF DESCRIPTION OF THE DRAWINGS

These and other aspects, features, and advantages of the invention will be apparent and elucidated from the following description of embodiments of the present invention, reference being made to the accompanying drawings, in which.

DESCRIPTION OF EMBODIMENTS

Figure 1:
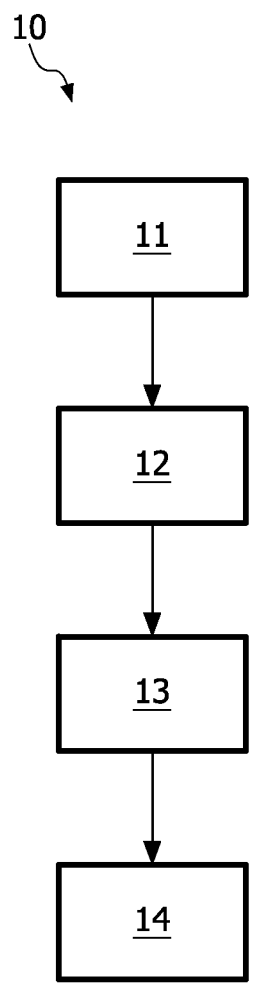
FIG. 1 is a block diagram of a system according to an embodiment.

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The present invention in some embodiments provides a therapy-planning method for combined treatment with a necrosis-inducing modality and necrosis-targeting agent. Hence, the method considers the influence of one treatment on the other, resulting in a prediction of the overall effect of the whole treatment.

Moreover, in some embodiment the present invention describes a method of determining and fine-tuning the effect of a combined treatment consisting of a necrosis induction by overheating or overcooling of human tissue and a subsequent administration of a radioactive necrosis-targeting agent. The mechanisms that lead to a local temperature increase or decrease are well known and analyzed in detail. The present invention in some embodiments utilizes this information together with additional knowledge of tissue properties, such as properties derived from diagnostic imaging, such as Computed Tomography, Magnetic Resonance Imaging, and Ultrasound Imaging, in the adjacency of the target region, to provide a patient-specific model of heat transport and a calculation of the temperature distribution in the respective tissue.

Necrosis-inducing therapies often exploit the sensitivity of cells to temperatures higher than about 50° C. or lower than 0° C. If cells are exposed to such extreme temperatures, they pass into uncontrolled cell death and literally fall apart, exposing their interior to the environment. Local heating above about 50° C. is caused by methods like high-intensity focused ultrasound (HIFU), electromagnetic or sonic fields, radiofrequency ablation (RFA), laser ablation, and microwave ablation (MWA), and results in coagulative necrosis, whereas local freezing of tissue below 0° C. is caused by direct contact through cryosurgery with a cryoprobe. At low temperatures, ice crystals formed inside the adjacent cells can tear them apart. More damage occurs when blood vessels supplying the diseased tissue freeze.

The following description focuses on embodiments of the present invention applicable to therapy planning and in particular to the planning of combined treatments with a necrosis-inducing modality and a targeted radiotherapy modality that uses a necrosis-targeting agent.

In some embodiments, the necrosis-inducing modality induces necrosis by heating or cooling (HC), and the targeted radiotherapy modality is a targeted, internal radiotherapy, such as tumor-necrosis therapy (TNT).

Currently, predictive algorithms to be used in therapy planning exist for HC as well as TNT. In the case of HC the algorithms include the calculation of temperature fields induced by the necrosis-inducing therapy, and in the case of TNT the algorithms are based on the calculation of absorbed radiation dose in the tissue. However, there are currently no combined therapy planning methods for HC and TNT in which the therapy modalities are interconnected to optimize the treatment effect.

In some embodiments, the invention provides a combined HC-TNT therapy planning taking into account the interactions between the two therapy modalities.

In an embodiment, according to FIG. 1, a system for combined therapy planning of a patient is provided. The system comprises:

a first calculation unit (11) for calculating a predicted temperature distribution in a target region and risk region of a tissue of the patient, a second calculation unit (12) for calculating a necrosis probability map based on the predicted temperature distribution of the tissue, indicating the damage resulting from a necrosis-inducing therapy, a third calculation unit (13) for calculating a biodistribution map of a necrosis-targeting agent comprising a radioactive substance intended to be added to the tissue on the basis of the necrosis probability map, and a fourth calculation unit (14) for calculating the radioactive dose distribution of the necrosis-targeting agent, e.g. by convolving the biodistribution map with a convolution kernel specific to the necrosis-targeting agent. An advantage of this embodiment is that the combined therapy planning in this integrated approach will lead to a patient-specific, effective way of treatment with reduced discomfort for the patient.

The term risk region used in this context denotes a region of normal tissue that is affected accidentally by the thermal or radiation energy used in the therapy and that should be protected from damage as much as possible during therapy.

The term target region denotes a region of diseased tissue that should be destroyed by thermal or radiation energy as completely as possible, subject to the boundary condition of limited damage to the risk tissue. In some embodiments, the target and risk regions are defined by a physician and in other embodiments by an algorithm, e.g. an algorithm based on threshold-based delineation and/or gradient-based delineation.

For different healthy tissue types, threshold values for thermal or radiation energy, beyond which the risk of damage to this tissue exceeds an acceptable level, are known from empirical studies. For diseased tissues, threshold values, which must be exceeded in order to achieve an acceptable level of treatment success, are known. One important step in image-based therapy planning is the delineation of tissues as risk and target tissues. The therapy-planning algorithm will use the threshold values to calculate a proposed treatment scheme/plan.

The delineation itself is performed either interactively on the image datasets by a physician or by the use of dedicated algorithms evaluating e.g. grey-values or gradients in the images.

Necrosis-inducing therapy induces necrosis through over-heating or over-cooling. However, an entire affected region of cells will reach full necrosis when the temperature is above an upper temperature threshold in the case of over-heating or when the temperature is below a lower temperature threshold in the case of over-cooling. In an intermediate temperature range, the fraction of necrotic cells will be lower than 100%. The expected fraction of necrotic cells in a certain region is called necrosis probability and the plot of the 2D or 3D distribution of necrosis probability values is consequently called necrosis probability map.

When the spatial and temporal temperature distribution within the treatment region has been calculated, this information is used to determine a necrosis probability map. Different models and tissue data sets for the determination of necrosis from temperature distributions are available. One example showing the dependence of necrosis probability on temperature increase can be found in FIG. 9 from Nathan J. McDannold, Natalia I. Vykhodtseva, Kullervo Hynynen: *Microbubble Contrast Agent with Focused Ultrasound to Create Brain Lesions at Low Power Levels: MR Imaging and Histologic Study in Rabbits*, Radiology: Volume 241: Number 1—October 2006.

A theoretical model often used to describe thermal damage to tissues is the Arrhenius damage integral approach, e.g. given in Equation 3 of Isaac A. Chang and Uyen D. Nguyen: *Thermal modeling of lesion growth with radiofrequency ablation devices*, BioMedical Engineering OnLine 2004, 3:27. The Arrhenius formulation serves to calculate a damage probability from the amount of absorbed heat energy and may be employed in this step.

The term "temperature distribution" in this context denotes the spatial distribution of temperature at one or several points in time. In many calculation schemes, this distribution will only be evaluated in a finite number of positions located on a (calculation) grid.

In an embodiment, the calculation of the damage due to necrosis-inducing therapy is based on calculating a temperature distribution in the target and risk regions and additional information comprised in the image dataset. Heat is transported in the patient's body from its position of generation to other locations. The underlying mechanisms consist mainly of heat conduction and convection and are described in the bioheat equation. The amount of heat in a small volume of the patient leads to a certain temperature at this position. The temperature distribution may be based, according to some embodiments, on the commonly known bioheat equation which expresses two mechanisms for heat flow in a tissue, namely thermal conduction, being the transmission of heat across matter, and thermal convection, being the transfer of heat by a flow of a fluid, such as blood perfusion. Factors that influence the thermal heat flow may be, for example, the thermo-physical properties of the tissue, such as its heat capacity, thermal conductivity, etc., the geometry of the irradiated organism, the heat production through absorption of light, such as laser light, the heat production owing to metabolic processes, the heat flow due to the perfusion of blood, and thermoregulatory mechanisms.

The bioheat equation may be defined as follows for an image-based patient-specific model of the target region and its surroundings:

$$\nabla(k\nabla T) + w_b c_b (T_a - T) + q_m + q_s = \rho c_p \frac{\partial T}{\partial t}.$$

Here k is the thermal conductivity of the tissue, T is the temperature, and $\nabla$ is the gradient vector $$\begin{pmatrix} \partial/\partial x \\ \partial/\partial y \\ \partial/\partial z \end{pmatrix}.$$

$w_b$ is the blood perfusion in units of kg/(s m$^3$), $c_b$ is the specific heat capacity of the blood, $T_a$ is the arterial temperature, $q_m$ is the metabolic heat generation, $q_s$ is the additional heat source or drain, $\rho$ is the tissue density, $c_p$ is the heat capacity of the tissue, and t is time. Typical values for the parameters are k=0.5 W/(m K), $c_p$=3750 J/(kg K), $\rho$=1000 kg/m$^3$, $c_b$=3640 J/(kg K) and $T_a$=37° C. If $w_b$ equals zero, no blood perfusion exists and hence there are no functioning blood vessels in the investigated tissue region. If, however, $w_b$ is greater than zero, there are blood vessels in the investigated tissue region.

The patient-specific model describes the spatial distribution of underlying parameters for the temperature, necrosis, and/or dose calculation. The spatial distribution of parameters is extracted from patient images and used in the calculation. Accordingly, the spatial distribution of the parameters k and $c_p$ and the location of the large blood vessels may be extracted from images and make the model patient-specific. Alternatively, standard models for males, females, adults, or infants are available for different calculation schemes that do not take into account the respective patient geometry.

In an embodiment in which the image dataset is acquired from Computed Tomography (CT), the spatial distribution of the heat-transporting vessels and the tissue property $c_p$ may be derived from the image dataset Large vessels may be identified in the image datasets and may be assigned a typical arterial or venous blood flow value. The microvasculature which is too small to be identified and to be explicitly modeled in the thermal simulation may be described by a modification of the thermal conductivity k to an effective conductivity $k_{eff}$ (see e.g. J Crezee and J J W Lagendijk: *Experimental verification of bioheat transfer theories: measurement of temperature profiles around large artificial vessels in perfused tissue*, Phys. Med. Biol., 1990, Vol. 35, No 7, 905-923).

Table 1 below shows the thermo physical properties of human tissue and water. Table 1 is adapted from A. F. Emery and K. M. Sekins (1982); K. Giering et al. (1995). The different tissue types may be identified in the image datasets and based on anatomical knowledge, and the respective geometrical distribution of parameters may be entered into the patient-specific model of heat transport.

TABLE 1

| Material | Conductivity (W m$^{-1}$ K$^{-1}$) | Density (kg m$^{-3}$) × 10$^{-3}$ | Specific heat (kJ kg$^{-1}$ K$^{-1}$) | Diffusivity (m$^2$ s$^{-1}$ × 10$^7$) |
|---|---|---|---|---|
| Muscle | 0.38-0.54 | 1.01-1.05 | 3.6-3.8 | 0.90-1.5 |
| Fat | 0.19-0.20 | 0.85-0.94 | 2.2-2.4 | 0.96 |
| Kidney | 0.54 | 1.05 | 3.9 | 1.3 |
| Heart | 0.59 | 1.06 | 3.7 | 1.4 |
| Liver | 0.57 | 1.05 | 3.6 | 1.5 |
| Brain | 0.16-0.57 | 1.04-1.05 | 3.6-3.7 | 0.44-1.4 |
| Water @ 37° C. | 0.63 | 0.99 | 4.2 | 1.5 |

In an embodiment, the temperature distribution is calculated on a 3D image dataset, resulting in a three-dimensional temperature propagation model.

In an embodiment, the physician will enter the treatment parameters of the necrosis-inducing modality into the planning system. The system will calculate the temperature field, the necrosis probability map, the biodistribution, and the additional therapeutic effect of the necrosis-targeting agent, as they will result from the chosen settings.

In another embodiment, temperature thresholds to be reached in the course of the heating/cooling therapy will be assigned to different regions of the treatment area based on the prior delineation of target and risk tissues. The planning system will calculate the total therapeutic effect of the HC and TNT therapy for a number of predefined treatment parameter sets of the necrosis-inducing modality and suggest the use of the parameter set which results in the closest approximation to the treatment goals.

In another embodiment, the thermal and internal dosimetry models are formulated such that the therapeutic goals are used as an input for an optimization algorithm, and the algorithm finds out the proper treatment planning parameters. This is the case, for example, in external radiation therapy planning. This embodiment provides that an accurate set of treatment parameters will be calculated fully automatically.

In an embodiment, the temperature distribution generated during the necrosis-inducing therapy is monitored by means of Magnetic Resonance Imaging (MRI). MRI can extract or compute the temperature distribution of the tissue with high precision. One approach of MRI-based thermometry is the so-called resonance frequency shift method (see e.g. Johan Olsrud: *MRI thermometry in phantoms by use of the proton resonance frequency shift method: application to interstitial laser thermotherapy*, Phys. Med. Biol. 43 (1998) 2597-2613), in which temperatures can be determined non-invasively with an error of less than 1 degree. The temperature distributions determined with such a map may be translated by means of, for example, the Arrhenius damage integral into a necrosis probability map, which in its turn represents the input data for the subsequent simulation of the TNT therapy effect.

In an embodiment, the calculation of the necrosis probability map is based on the temperature distribution in conjunction with a planning objective. The planning objective serves to formulate optimization criteria. In the case of heating, for example, the temperature of target regions must be above a minimum temperature $T_{min,heat}$, and the temperature of tissue at risk must be below a maximum temperature $T_{max,heat}$. In the case of cooling, the temperature of target regions must be below a maximum temperature $T_{max,cool}$, and the temperature of tissue at risk must be above a minimum temperature $T_{min,cool}$. The necrosis probability map indicates the necrosis probability of the tissue comprised in the target and risk regions. The necrosis probability map may be obtained either from empirical data on the relation between temperature and necrosis probability or by using a tissue damage model, e.g. the Arrhenius damage integral.

In an embodiment, the necrosis probability map is used in the calculation of the bio-distribution of the necrosis-targeting agent. The 'biodistribution' is the spatial concentration distribution of a diagnostic or therapeutic agent, such as the necrosis-targeting agent, within the body. Another term describing the biodistribution is "uptake". In an embodiment, the necrosis probability map is converted into a map of uptake and biodistribution of a radio-labeled necrosis-targeting agent. The uptake of the agent in each voxel of a diagnostic image is a function of the necrosis probability, but also depends on parameters such as the distance of the voxel to the surface of the tissue comprised in the diagnostic image or to blood-supplying vessels of the necrotic region. One algorithm for converting the necrosis probability density p(r) in units of [cm$^{-3}$], ranging from 0% to 100%, to a biodistribution A(r) of an injected TNT agent activity $A_{inj}$ is as follows:

$$A(r)=p(r)*A_{inj}/P$$

where P denotes the integral of p(r) over the entire patient volume.

In an embodiment, the biodistribution of the TNT therapeutic agent is imaged by a SPECT or PET procedure with a tracer, i.e. diagnostic, amount of the substance (e.g. Cotara is labeled with I-131, which can be seen in SPECT). These biodistribution images may be taken, instead of the biodistributions estimated from the necrosis probability map, as the basis for the radioactive dose calculation.

The dose and manner of administration has to be determined in order to be able to calculate the additional effect of the necrosis targeting agent.

In an embodiment, the biodistribution is subsequently used in the calculation of the necessary dosage and/or in determining a manner of application of the necrosis-targeting agent, and its additional impact is compared with the necrosis-inducing modality alone. The effect of the TNT treatment on tissue may be estimated from the so-called tumor control probability (TCP) and normal tissue complication probability (NTCP) curves as they are known from radiation biology research for most tissue types. The additional effect thus calculated may be added to the therapeutic effect of the necrosis-inducing modality to obtain the total therapy effect. The total effect calculated by assuming different dosages of the TNT agent may be compared with the therapy requirements and the best match may be chosen.

In an embodiment, the radioactive dose distribution is calculated by convolving the biodistribution with a targeting agent specific convolution kernel. The absorption pattern of radiation energy may be described by a convolution of the distribution of radioactivity with a kernel specific to the therapeutic isotope in use. One realization of this calculation scheme is the so-called voxel-based S-value approach. This approach models the absorption of a radioactive dose by employing transfer values of activity in one location to absorbed dose in other locations. The description results in a dose-volume kernel containing the so-called voxel-based S-values; the activity distribution must be convoluted with this kernel in order to obtain the radioactive dose distribution. The convolution kernel is adapted to the physical properties of the targeting agent, such as linear energy transfer (LET) which is equal to the energy dE, which a charged particle loses when traveling a distance dl. The convolution kernel moreover depends on the biological properties of the agent, such as the residence time in necrotic tissue, meaning the average time the necrosis-targeting agent spends within the necrotic tissue, and on the manner in which the agent is administered, such as through the Radio Frequency ablation catheter directly into the lesion. The kernel depends only on the type of radioisotope used, such as Iodine-131, and may be found pre-calculated e.g. in commonly known Medical Internal Radiation Dose (MIRD) pamphlets, or may be calculated with high precision e.g. by Monte-Carlo simulation of a point source of the isotope and tallying of the deposited energy in the neighborhood of this source.

In an embodiment, the biodistribution map is computed from Single Photon Emission Computed Tomography biodistribution imaging.

The additional therapeutic effect of the necrosis-targeting agent may then be calculated by the following sequence of steps: Firstly, the observed or predicted biodistribution of the necrosis-targeting agent is converted into a distribution of absorbed radiation energy, e.g. by the above-mentioned kernel method. Secondly, the absorbed energy map is converted into a therapeutic effect map by the use of e.g. Tissue Complication Probability (TCP) and Normal Tissue Complication Probability (NTCP) curves for the specific tissue types. This therapeutic effect of the TNT step may be added to the estimated or observed therapeutic effect of the HC step.

In an embodiment, the system comprises a feedback unit that processes real treatment results and predicted results. The feedback unit may be used when e.g. the HC treatment results in a necrosis distribution that does not acceptably correspond to the predicted necrosis distribution. The feedback unit is then configured to adjust the computation of the next necrosis distribution on the basis of the information. In another embodiment, the feedback unit is configured to compare the real therapeutic effect with the predicted therapeutic effect on the basis of the calculated therapy dosage plan.

In a practical implementation, the invention in some of its embodiments will be used in clinical settings. Before the treatment of small cancerous lesions, such as metastases in the liver or the brain, acquired image data of the patient are utilized by the therapy-planning method to create the necrosis probability map. The therapy-planning method calculates a suggested necrosis distribution of the target region from the definition of risk and target regions and the necrosis probability map. The necrosis distribution is the real spatial distribution of necrotic cells in the patient caused by a therapy step or existing as a disease condition. In some embodiments, the physician may optionally alter the necrosis distribution. Subsequently, the therapy planning method calculates an estimated radioactive dose distribution caused by a necrosis-targeting agent based on the necrosis distribution.

In an embodiment, the necrosis-targeting agent is radiolabeled.

In an embodiment, the necrosis-targeting agent comprises an $I^{131}$ isotope. Other necrosis-targeting agents may also be possible.

In an embodiment, the necrosis-targeting agent is a radioactive isotope, such as a labeled isotope (?) adapted to a targeting antibody.

In some embodiments, the present invention allows the physician a detailed planning of the treatment and an estimation of its therapy success before the actual intervention starts, thus resulting in higher cost effectiveness and success rate of the therapy.

The first, second, third, and fourth calculation unit may be any unit normally used for performing the relevant tasks, e.g. an item of hardware such as a processor with a memory. The processor may be any of a variety of processors, such as Intel or AMD processors, CPUs, microprocessors, Programmable Intelligent Computer (PIC) microcontrollers, Digital Signal Processors (DSP), etc. However, the scope of the invention is not limited to these specific processors. The memory may be any memory capable of storing information, such as Random Access Memories (RAM) like Double Density RAM (DDR, DDR2), Single Density RAM (SDRAM), Static RAM (SRAM), Dynamic RAM (DRAM), Video RAM (VRAM), etc. The memory may also be a FLASH memory such as a USB, Compact Flash, SmartMedia, MMC memory, MemoryStick, SD Card, MiniSD, MicroSD, xD Card, TransFlash, and MicroDrive memory, etc. However, the scope of the invention is not limited to these specific memories.

The system may further be provided with a display, such as a touch screen display, adapted to define the target and risk regions and to present the temperature distribution map, necrosis probability map, biodistribution map, etc.

In an embodiment, the system is comprised in a medical workstation or medical system, such as a Computed Tomography (CT) system, Magnetic Resonance Imaging (MRI) System, or Ultrasound Imaging (US) system.

Figure 2:
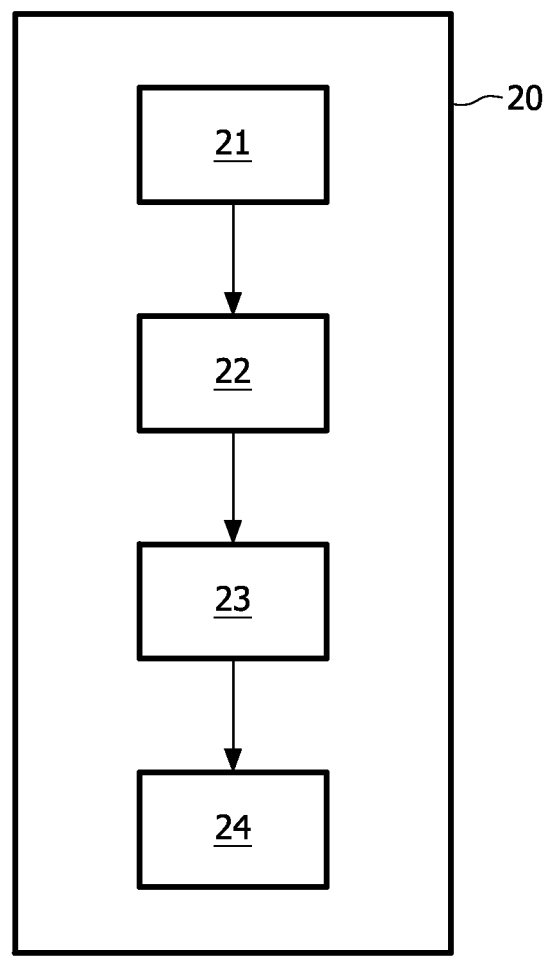
FIG. 2 is a block diagram of an method according to an embodiment.

In an embodiment as shown in FIG. 2, a method 20 is provided. The method comprises the steps of:

calculating 21 a predicted temperature distribution in the patient's tissue, calculating 22 a necrosis probability map based on the predicted temperature distribution of the tissue, calculating 23 a biodistribution map of a necrosis-targeting agent comprising a radioactive substance intended to be added to the tissue on the basis of the necrosis probability map, and calculating 24 the radioactive dose distribution of the necrosis-targeting agent by convolving the biodistribution map with a convolution kernel specific to the necrosis-targeting agent.

Figure 3:
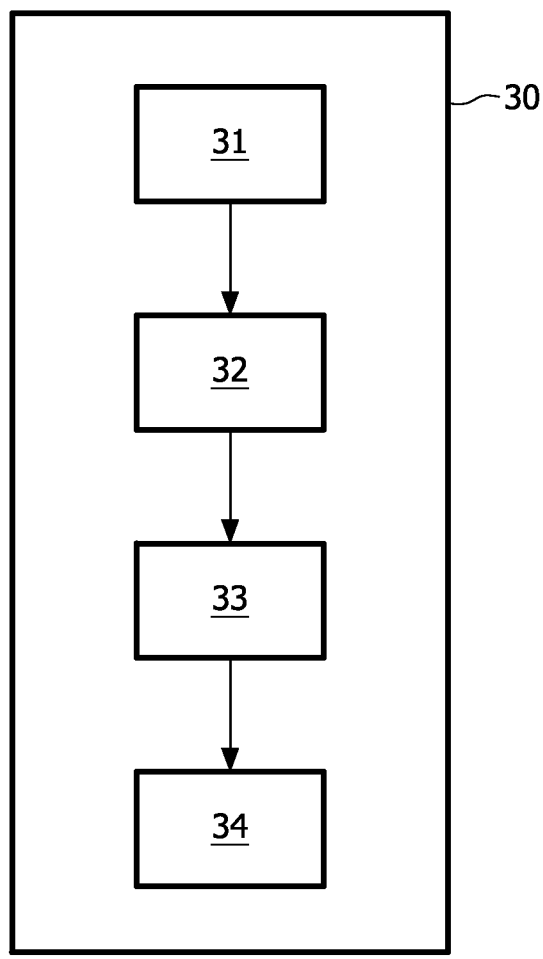
FIG. 3 is a block diagram of a computer-readable medium according to an embodiment.

In an embodiment as shown in FIG. 3, a computer-readable medium 30 having embodied thereon a computer program for combined therapy planning to be processed by a processor is provided. The computer program comprises:

a first calculation code segment 31 for calculating a predicted temperature distribution in the patient's tissue, a second calculation code segment 32 for calculating a necrosis probability map based on the predicted temperature distribution of the tissue, a third calculation code segment 33 for calculating a biodistribution map of a necrosis-targeting agent comprising a radioactive substance intended to be added to the tissue on the basis of the necrosis probability map, and a fourth calculation code segment 34 for calculating the radioactive dose distribution of the necrosis-targeting agent by convolving the biodistribution map with a convolution kernel specific for the necrosis-targeting agent.

In an embodiment, the computer-readable medium comprises code segments arranged, when run by an apparatus having computer processing properties, for performing all of the method steps defined in some embodiments.

In an embodiment, a use of the system, method, or computer-readable medium for therapy planning in the treatment of cancer or neoplasia is provided.

In an embodiment, the system according to some embodiments is comprised in a medical workstation.

The invention may be implemented in any suitable form including hardware, software, firmware, or any combination of these. However, the invention is preferably implemented as computer software running on one or more data processors and/or digital signal processors. The elements and components of an embodiment of the invention may be physically, functionally, and logically implemented in any suitable way. Indeed, the functionality may be implemented in a single unit, in a plurality of units, or as part of other functional units. As such, the invention may be implemented in a single unit or may be physically and functionally distributed over different units and processors.

Although the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements, or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A system for planning a combined necrosis-inducing and -targeting therapy of a patient, said system comprising:
    a first calculation processor for calculating a predicted temperature distribution in the patient's tissue resulting from a necrosis-inducing modality,
    a second calculation processor for calculating a necrosis probability map based on said predicted temperature distribution of said tissue,
    a third calculation processor for calculating a biodistribution map of a necrosis-targeting agent comprising a radioactive substance intended to be added to said tissue on a basis of said necrosis probability map, and
    a fourth calculation processor for calculating a radioactive dose distribution of said necrosis-targeting agent by convolving the biodistribution map with a convolution kernel specific to said necrosis-targeting agent.

2. The system according to claim 1, wherein said temperature distribution is based on a patient-specific model of heat transport comprising tissue properties extractable from an image dataset of a tissue of said patient.

3. The system according to claim 2, wherein said image dataset comprises a target region and a risk region.

4. The system according to claim 2, wherein said image dataset is acquired by an image acquisition apparatus based on Computed Tomography, Magnetic Resonance Imaging, Positron Emission Spectroscopy, or Single Photon Emission Spectroscopy.

5. The system according to claim 1, wherein said probability map indicates the damage resulting from a necrosis-inducing therapy, wherein said necrosis-inducing therapy pertains to necrosis induction by thermal heating or cooling of tissue.

6. The system according to claim 1, wherein the necrosis-targeting agent is 131I-chTNT-1/B.

7. The system according to claim 1, wherein the necrosis-targeting agent is a radioactive isotope adapted to a targeting antibody.

8. The system according to claim 3, wherein said target region and/or risk region are/is defined either by software or by a human.

9. The system according to claim 1, wherein said target region and/or said risk region are/is defined on the basis of a predetermined temperature limit for the temperature of the target region and for the temperature of the risk region.

10. The system according to claim 1, wherein said necrosis probability map is a 2D or 3D image or sequence of images of expected density probability of necrotic cells in said target region and risk region, due to said necrosis-inducing therapy.

11. The system according to claim 2, wherein said temperature distribution is calculated from a bio heat equation which is part of said patient-specific model.

12. The system according to claim 1, wherein the radiobiological or therapeutic effect and risk to healthy tissue due to the necrosis-targeting agent is calculated from Tissue Complication Probability or Normal Tissue Complication Probability curves and from said calculated dose distribution.

13. The system according to claim 1, wherein said convolution kernel is adapted to the physical properties of the targeting agent.

14. The system according to claim 1, further comprising a feedback unit configured to compare real treatment result with calculated predicted treatment result, and to fine-tune calculations performed by the first, second, and third calculation processors.

15. The system according to claim 1 being comprised in a medical workstation.

16. The system according to claim 1, wherein said predicted temperature distribution is computed on the basis of Magnetic Resonance Imaging Thermometry.

17. The system according to claim 1, wherein said biodistribution map is computed on the basis of Single Photon Emission Computed Tomography biodistribution imaging.

18. A method (20) of planning a combined necrosis-inducing and -targeting therapy of a patient, comprising:
    calculating, by a first processor, a predicted temperature distribution in the patient's tissue resulting from a necrosis-inducing modality,
    calculating, by a second processor, a necrosis probability map based on said predicted temperature distribution of said tissue,
    calculating, by a third processor, a biodistribution map of a necrosis-targeting agent comprising a radioactive substance intended to be added to said tissue on a basis of said necrosis probability map, and
    calculating, by a fourth processor, a radioactive dose distribution of said necrosis-targeting agent by convolving the biodistribution map with a convolution kernel specific to said necrosis-targeting agent.

19. A non-transitory computer-readable medium having embodied thereon a computer program designed to be processed by a processor for planning a combined necrosis-inducing and -targeting therapy of a patient, said computer program comprises:
    a first calculation code segment for calculating a predicted temperature distribution in the patient's tissue resulting from a necrosis-inducing modality,
    a second calculation code segment for calculating a necrosis probability map based on said predicted temperature distribution of said tissue,
    a third calculation code segment for calculating a biodistribution map of a necrosis-targeting agent comprising a radioactive substance intended to be added to said tissue on a basis of said necrosis probability map, and
    a fourth calculation code segment for calculating a radioactive dose distribution of said necrosis-targeting agent by convolving the biodistribution map with a convolution kernel specific to said necrosis-targeting agent.

* * * * *